(12) United States Patent
Graupner

(10) Patent No.: US 7,605,185 B2
(45) Date of Patent: Oct. 20, 2009

(54) TREATMENT OF ARRHYTHMIA BY RETINOIDS AFFECTING SIGNAL TRANSDUCTION

(76) Inventor: Gerhart Graupner, P.O. Box 710475, San Diego, CA (US) 92171

( * ) Notice: Subject to any disclaimer, the term of this patent is extended or adjusted under 35 U.S.C. 154(b) by 180 days.

(21) Appl. No.: 11/062,222

(22) Filed: Feb. 17, 2005

(65) Prior Publication Data

US 2005/0171202 A1 Aug. 4, 2005

Related U.S. Application Data

(63) Continuation-in-part of application No. 10/155,307, filed on May 22, 2002, now abandoned, which is a continuation of application No. PCT/US2000/042233, filed on Nov. 22, 2000.

(60) Provisional application No. 60/167,438, filed on Nov. 23, 1999.

(51) Int. Cl.
*A61K 31/07* (2006.01)
*A61K 31/56* (2006.01)

(52) U.S. Cl. ............... 514/725; 514/168; 514/821

(58) Field of Classification Search ............... None
See application file for complete search history.

(56) References Cited

U.S. PATENT DOCUMENTS

| 5,124,313 A | 6/1992 | Schaeffer et al. ............ 514/2 |
| 5,968,981 A | 10/1999 | Chien et al. ............ 514/557 |
| 6,221,618 B1 | 4/2001 | Chien et al. ............ 435/7.21 |
| 6,358,697 B2 | 3/2002 | Rothenberg et al. ...... 435/7.21 |

OTHER PUBLICATIONS

Armstrong et al., 13-cis retinoic acid and isomerization in paediatric oncology is changing shape the key to success?, 2005, Biochemical Pharmacology, vol. 69, pp. 1299-1306.*
Gottardis et al., The efficacy of 9-cis retinoic acid in experimental models of cancer, 1996, Breast Cancer Research and Treatment, vol. 38, pp. 85-96.*
Giguere, Vincent, "Retinoic Acid Receptors and Cellular Retinoid Binding Proteins: Complex Interplay in Retinoid Signaling", J. Endocrine Society, Aug. 1994, pp. 61-79, vol. 15, No. 1, USA.
Kuno, Shin-Ichi et al., "Outgrowth of pseudopodial cables induced by all-trans retinoic acid in micromere-derived cells isolated from sea urchin embryos", Develop. Growth Differ., 1999, pp. 193-199, vol. 41, Japan.
Allikmets, Rando et al., "A photoreceptor cell-specific ATP-binding transporter gene (ABCR) is mutated in recessive Stargardt macular dystrophy", Nature Genetics, Mar. 1997, pp. 236-246, vol. 15.
James, Thomas N., M.D., "Normal and Abnormal Consequences of Apoptosis in the Human Heart From Postnatal Morphogenesis to Paroxysmal Arrhythmias", Circulation, Jul. 1994, pp. 556-573, vol. 90, No. 1, Texas, USA.
Decottignies, Anabelle et al., "Complete Inventory of the yeast ABC proteins", Nature Genetics, Feb. 1997, pp. 137-145, vol. 15.
Lee, K. et al., "Ciclazindol Inhibits ATP-Sensitive K+ Channels and Stimulates Insulin Secretion in CRI-G1 Insulin-Secreting Cells", Molecular Pharmacology, 1996, pp. 715-720, vol. 49,USA.
Demolombe, Sophie et al., "ATP-binding cassette proteins as targets for drug discovery", TiPS, Aug. 1996, pp. 273-275, vol. 17, USA.
Ämmälä, Carina et al., "Promiscuous coupling between the sulphonylurea receptor and inwardly rectifying potassium channels", Feb. 8, 1996, pp. 545-548, vol. 379, USA.
Kolaczkowski, Marcin et al., "Anticancer Drugs, Ionophoric Peptides, and Steroids as Substrates of the Yeast Multidrug Transporter Pdr5p", The Journal of Biological Chemistry, Dec. 6, 1996, pp. 31543-31548, vol. 271, No. 49, USA.
Notsu, T. et al., "Block of ATP Regulated K+ Channels by Sodium 5-Hydroxydecanoate, A new Antiarrhythmic Agent, In Isolated Guinea-Pig Heart Cells", J. Mol Cell Cardiol., 1989, pp. S.9, Supplement II, Abstract 27, USA.
Luciani, Marie-Francoise et al., "The ATP binding cassette transporter ABC1, is required for the engulfment of corpses generated by apoplotic cell death". The EMBO Journal, 1996, pp. 226-235, vol. 15, No. 2, USA.
Kralli, Anastasia et al., "An FK506-sensitive Transporter Selectively Decreases Intracellular Levels and Potency of Steroid Hormones", The Journal of Biological Chemistry, Jul. 19, 1996, pp. 17152-17156, vol. 271, No. 29, USA.
Abbott, Geoffrey W. et al., "MiRP1 Forms Ikr Potassium Channels with HERG and Is Associated with Cardiac Arrhythmia", Cell Press, Apr. 16, 1999, pp. 175-187, vol. 97, USA.
Tucker, Stephen J. et al., "Truncation of Kir6.2 produces ATP-sensitive K+ channels in the absence of the sulphonylurea receptor", Nature, May 8, 1997, pp. 179-183, vol. 387, USA.
Gribble, Fiona M. et al., "Tissue Specificity of Sulfonylureas—Studies on Cloned Carida and •-Cell KATP Channels", Diabetes, Sep. 1998, pp. 1412-1418, vol. 47, USA.
Zona, Cristina et al., "Arachidonic acid augments potassium currents in rat neocortical neurones", Molecular Neuroscience, Apr. 1993, pp. 359-362, vol. 4, No. 4, USA.
Smith-Thomas, Linda et al., "Effects of Isotretinoin on the Behavior of Neural Crest Cells in Vitro", Brief Notes, 1987, pp. 276-281; USA.
Lu, Xian-Ping et al., "Novel retinoid-related molecules as a apoptosis inducers and effective inhibitors of human lung cancer cells in vivo", Nature Medicine, Jun. 1997, pp. 686-690, vol. 3, USA.
Janick-Buckner, D. et al., "Induction of HL-60 cell differentiation by water-soluable and nitrogen-containing conjugates of retinoic acid and retinol", The FASEB Journal, Mar. 1991, pp. 320-325, vol. 5, USA.

(Continued)

*Primary Examiner*—Robert Landsman
*Assistant Examiner*—Ian Dang
(74) *Attorney, Agent, or Firm*—Fitch, Even, Tabin & Flannery

(57) ABSTRACT

A polypeptide is identified as being functionally included in a signal transduction pathway having a biological effect. Contemplated polypeptides are different from a retinoic acid receptor, a retinoid X receptor, or a cellular retinoic acid binding protein, however bind a retinoid or retinoid metabolite, and binding of the retinoid or retinoid metabolite lead to a modulation of the biological effect. In particularly contemplated methods, a retinoid or retinoid metabolite is administered to a cell or mammal in a concentration effective to modulate the biological effect.

2 Claims, 4 Drawing Sheets

OTHER PUBLICATIONS

Bissonnette, Reid P. et al., "9-cis Retinoic Acid Inhibition of Activation-Induced Apoptosis Is Mediated via Regulation of Fas Ligand Requires Retinoic Acid Receptor and Retinoid X Receptor Activation", Molecular and Cellular Biology, Oct. 1995, pp. 5576-5585, vol. 15, No. 10, USA.

Wang, Xin et al., "Retinoic acid up-regulates ciliary neurotrophic factor receptors in cultured chick neurons and cariomyocytes", Neuroscience Letters, 1998, pp. 9-12, USA.

Kitabayashi, Issay et al., "A Novel Pathway For Retinoic Acid-Induced Differentiation of F9 Cells That Is Distinct From Receptor-Medciated Trans-Activation", In Vitro Cell Dev. Bio., Nov. 1994, pp. 761-768, USA.

Davis, W.L. et al., "Changes in cytosolic calcium, bleb formation, and cell death in neural crest cells treated with isotretinoin and 4-oxo-isotretinoin", Abstract—Journal of Craniofacial Genetics & Developmental Biology, Apr.-Jun. 1991, pp. 105-118, vol. 11, No. 2, USA.

Willnow, Thomas E. et al., "Lipoprotein receptors: new roles for ancient proteins", Nature Cell Biology, Oct. 1999, pp. E157-E162, vol. 1, USA.

Davis, Faith B. et al., "Retinoic Acid Inhibits Calmodulin Binding to Human Erythrocyte Membranes and Reduces Membrane CA2+-Adenosine Triphosphatase Activity", J. Clin. Invest., Jun. 1990, pp. 1999-2003, vol. 85, USA.

Vakiani, Efsevia et al., "Substrate Specificity and Kinetic Mechanism of the Insect Sulfotransferase, Retinol Dehydratase", The Journal of Biological Chemistry, Dec. 25, 1998, pp. 35381-35387, vol. 273, No. 52, USA.

Dousa, Thomas P. et al., "Modulation of renal Na-Pi cotransport by hormones acting via genomic mechanism and by metabolic factors", Kinney International, 1996, pp. 997-1004, vol. 49, USA.

Shao, Zhi-Ming et al., "p53 independent G0/G1 arrest and apoptosis induced by a novel retinoid in human breast cancer cells", Oncogene, 1995, pp. 493-504, vol. 11, USA.

Guo, Yuan et al., "All-trans retinol, vitamin D and other hydrophobic compounds bind in the axial pore of the five-stranded coiled-coil domain of cartilage oligomeric matrix protein", The EMBO Journal, 1998, pp. 5265-5272, vol. 17, No. 18, USA.

Pijnappel, W. W. M. et al., "The retinoid ligand 4-oxo-retinoic acid is a highly active modulator of positional specification", Nature, Nov. 1993, pp. 340-344, vol. 366, USA.

Kang, Jing X. et al., "Protective Effects of All-Trans-Retinoic Acid Against Cardiac Arrhythmias Induced by Isoproterenol, Lysophosphatidylcholine or Ischemia and Reperfusion", Journal of Cardiovascular Pharmacology, 1995, pp. 943-948, vol. 26, No. 6, USA.

Zhou, Ming Dong et al., "Retinoid-dependent pathways suppress myocardial cell hypertrophy", Proc. Natl. Acad. Sci., Aug. 1995, pp. 7391-7395, vol. 92, USA.

Abbott, Barbara D. et al., "Retinoic acid alters epithelial differentiation during palatogenesis", J. Craniofac Genet Dev. Bio., 1991, pp. 315-325, USA.

Lammer, Edward, "Preliminary observations on isotretinoin-induced ear malformations and pattern formation of the external ear", J. Craniofac Genet Dev. Bio., 1991, pp. 292-295, USA.

Bain, et al., "Retinoic Acid Promotes Neural and Represses Mesodermal Gene Expression in Mouse Embryonic Stem Cells in Culture"; Biochemical and Biophysical Research Communications 223, 691-694 (1996), Article No. 0957; Academic Press, Inc.

Bradford, et al., "Transcriptional Regulation adn increased Functional Expression of the Inositol Trisphosphate Receptor in Retinoic Acid-Treated HL-60 Cells", The Journal of Biological Chemistry, vol. 267, No. 29, Issue of Oct. 15, pp. 20959-20965, 1992, American Society for Biochemistry and Molecular Biology, Inc.

Kitabayashi, et al., "A Novel Pathway for Retinoic Acid-Induced Differentiation of F9 Cells that is Distinct from Receptor-Mediated Trans-Activation"; In Vitro Cell. Dev. Biol. 30A: 761-768, Nov. 1994; Society for In Vitro Biology.

* cited by examiner

TREATMENT OF ARRHYTHMIA BY RETINOIDS AFFECTING SIGNAL TRANSDUCTION

This application is a continuation-in-part of U.S. Ser. No. 10/155,307, filed May 22, 2002 which is a continuation of International application PCT/US00/42233, filed Nov. 22, 2000, and claims the benefit of U.S. provisional application Ser. No. 60/167,438, filed Nov. 23, 1999, the disclosures of all of which are expressly incorporated herein by reference.

FIELD OF THE INVENTION

The field of the invention is modulation of signal transduction.

BACKGROUND OF THE INVENTION

Many physiological and pathophysiological conditions can be influenced by presenting a cell, cell culture, or organism with a drug that directly or indirectly interferes with that condition. For example, drugs that directly interfere with a physiological and pathophysiological condition include enzyme inhibitors (e.g., penicillin inhibits bacterial transpeptidases, or lovastatin/MK-803 [Mevinolin™] inhibits 3-hydroxy-3-methylglutaryl coenzyme A reductase) or antisense nucleic acids (e.g., antisense DNA inhibit translation of viral genes). Although directly interfering drugs are often highly specific towards their target, their biological action is frequently limited to individual biochemical conversions or processes.

In order to modulate a plurality of biochemical reactions or physiological events, drugs that modulate signal transduction pathways may be employed, and numerous compositions and methods are known in the art to interfere with signal transduction pathways. For example, in one method of interfering with a signal transduction pathway, a signaling molecule (e.g., a cytokine or insulin) is added to a cell or organism. Adding signaling molecules is often advantageous, especially where exogenous addition to a system lacking the signaling molecule reconstitutes the physiologically normal level of the signaling molecule. However, addition of exogenous signaling molecules is frequently problematic, especially where the molecules are immunogenic peptides or peptide preparations with impurities and/or inhomogeneities.

Alternatively, receptors for the signaling molecules may be blocked or otherwise rendered functionally inactive. For example, a beta-blocker competitively inhibits binding of the natural signal adrenalin to beta-adrenergic receptors in the nervous system. Receptor blockers generally exhibit strong inhibition of their target receptors; however, tend to inhibit non-target receptors, especially where the non-target receptors belong to the same family as the target receptor (e.g., various beta-blockers tend to block non-target beta-2 receptors).

In another example, elements within a signaling cascade may be inhibited to prevent a signal from being transduced to the target compartment of a cell. A particularly promising element in a signaling cascade is the vascular endothelial growth factor (VEGF) receptor kinase, which specifically phosphorylates its substrate in dependence of binding of VEGF to the VEGF receptor, and it has recently been shown, that VEGF kinase inhibitors effectively inhibit signaling in VEGF kinase associated pathways [Drevs J. et al. Effects of PTK787/ZK 222584, a specific inhibitor of vascular endothelial growth factor receptor tyrosine kinases, on primary tumor, metastasis, vessel density, and blood flow in a murine renal cell carcinoma model. *Cancer Res* 2000; 60(17):4819-24]. However, even relatively low cross-reactivity with kinases other than VEGF kinases may potentially disrupt a plethora of non-targeted pathways due to the presence of various kinases in many other signaling pathways.

In a still further example, elements and processes at the end-point of a signaling cascade may be inhibited to prevent the signal from being translated into a regulatory or other function in the cell. A typical example of "end-point inhibition" is the use of antisense nucleic acids that hybridize with a transcription product that is being formed in a response to the signal, or that form triple helices with a target sequence that is activated by the signal.

Although there are various methods of interfering with signal transduction pathways known in the art, all or almost all of them suffer from one or more disadvantages. Therefore, there is a need to provide novel methods for interfering with signal transduction pathways.

Vitamin A-derivatives (retinoids) occur physiologically mostly in the form of retinol, retinaldehyde and retinoic acid. The latter was recognized as the form preventing vitamin deprivation conditions. Known mediators of retinoid effects on gene expression are transcription factors of the class II steroid/thyroid family: the retinoic acid receptors isoforms (RARalpha, RARbeta, RARgamma) which are inducible by all-trans RA, and the mammalian retinoid X receptor isoforms (RXRalpha, RXRbeta, RXRgamma) which are inducible by 9cis-RA. The general toxicity of retinoic acid and retinoids (Biesalski H K; Comparative assessment of the toxicology of vitamin A and retinoids in man, Toxicology 57, 117-161, 1989; Kamm et al. Preclinical and clinical toxicology of selected retinoids, the retinoids 2, p. 287-326, 1984) has been motivation to identify more selective retinoids. Aided by test systems of cells overexpressing distinct isoforms of RAR and/or RXR, it has become feasible to design and test novel retinoid agonists that display considerable receptor selectivity (see for example U.S. Pat. No. 6,096,787; Graupner et al., Biochem. Biophys. Res. Comm. 179(3): 1554-1561, 1991; Lehmann et al., Retinoids selective for retinoid X receptor response pathways, Science 258, 1944-1946, 1992). Further development in chemical derivatization generated receptor-selective antagonists for RAR or RXR, and also retinoids that allowed to dissociate receptor-mediated reporter gene activation from receptor-mediated gene repression (e.g. Chen et al., RAR-specific agonists/antagonists which dissociate transactivation and AP-1 transrepression inhibit anchorage-independent cell proliferation, EMBO J 14, 1187-1197, 1995), or receptor-selective agonists that are susceptible to geometric determinants of the promoter context, such as spacing of DNA recognition sites (Benoit G et al, RAR-independent RXR signaling induces t(15;17) leukemia cell maturation, EMBO J 18(24), 7011-7018, 1999). Most importantly, clinical trials with receptor-selective retinoids (Miller V A et al., Initial clinical trial of a selective retinoid X receptor ligand, LGD1069, J. Clin. Oncol. 15, 790-795, 1997) indicated that the toxicity profile of selective retinoids is different from the well-known toxicity profile of retinoic acid in humans as reported by Biesalski et al.; further development of highly receptor-selective compounds with rigid backbone structures did not generate a favorable toxicity profile. Therefore, it is desirable to develop retinoids that display a different repertoire of interactions, characterized by selectivity for non-receptor pathways that would be expected to be more cell-specific expected. Preferably, such retinoids would interfering selectively with signal transduction pathways. It is apparent from the literature that the cumulative toxicity after administration of cis-configured retinoid stereoisomers is different from the cumulative toxicity seen after administration of all-trans-configured retinoids. It is therefore important to appreciate that targets of all-trans retinoids are not the same as targets of cis-configured retinoids. Thus, the identification of a polypeptide target for all-trans-configured retinoids does not specify that the particular polypeptide is also a target of cis-configured retinoids.

SUMMARY OF THE INVENTION

The present invention is directed to compositions and methods of cell-specifically modulating a signal transduction pathway in a system. In one step, the signal transduction pathway is identified as functionally including a cellular polypeptide that binds a retinoid or retinoid metabolite, wherein the cellular polypeptide is not a retinoic acid receptor (RAR), retinoid X receptor (RXR), or a cellular retinoic acid binding protein (CRABP), and wherein binding of the retinoid or retinoid metabolite results in modulation of a biological effect modulated by the signal transduction pathway. In a further step, the retinoid or retinoid metabolite is administered to the system (e.g., a mammal, cell-, or tissue culture) in a concentration effective to modulate the biological effect.

In one aspect of the inventive subject matter, the retinoid has a cis-configuration and is preferably a 9-cis-retinoid, a 4-hydroxyphenyl-retinamide, or a 4-hydroxyphenyl-retinamide analog. Further contemplated retinoids and retinoid metabolites include sulfur-containing retinoids, and especially contemplated retinoid metabolites include a sulfated retinoid and S-adenosyl-retinoid.

In another aspect of the inventive subject matter, the cellular polypeptide comprises an ion channel, preferably with a specificity for $K^+$, $Ca^{2+}$, or $Na^+$, or a transmembrane transport protein, and it is particularly preferred that the ion channel, or the transmembrane transport protein, functionally cooperates with a mammalian member of the family of ATP-binding cassette proteins, such as the sulfonylurea receptor (SUR) or a related protein. It is further especially contemplated that the ion channel comprises an adenosine triphosphate (ATP) gated potassium channel complex.

In a further aspect of the inventive subject matter, contemplated biological effects are amplified by binding of the retinoid or retinoid metabolite, and particularly contemplated biological effects include cell growth, cell division, insulin secretion, prevention or interruption of cardiac arrythmia, support of cardiac repolarisation, support of memory function, prevention or interruption of depression, and interference with pathways leading to obesity.

In a still further aspect of the inventive subject matter, contemplated retinoids have a bimodal effect, and administration of the retinoid or retinoid metabolite at a first concentration modulates a first biological effect, and administration of the retinoid or retinoid metabolite at a second concentration modulates a second biological effect.

Various objects, features, aspects and advantages of the present invention will become more apparent from the following detailed description of preferred embodiments of the invention, along with the accompanying drawing.

BRIEF DESCRIPTION OF THE DRAWING

FIGS. 1A-1D depict exemplary retinoids and retinoid metabolites.

DETAILED DESCRIPTION

Figure 1B:
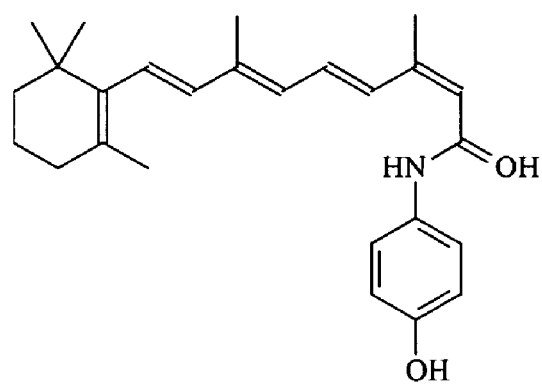
Figure 1C:
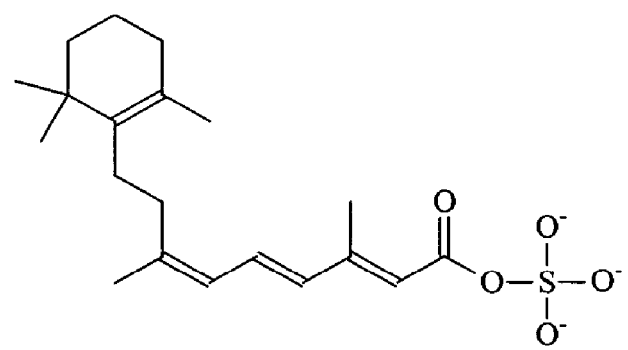
Figure 1D:
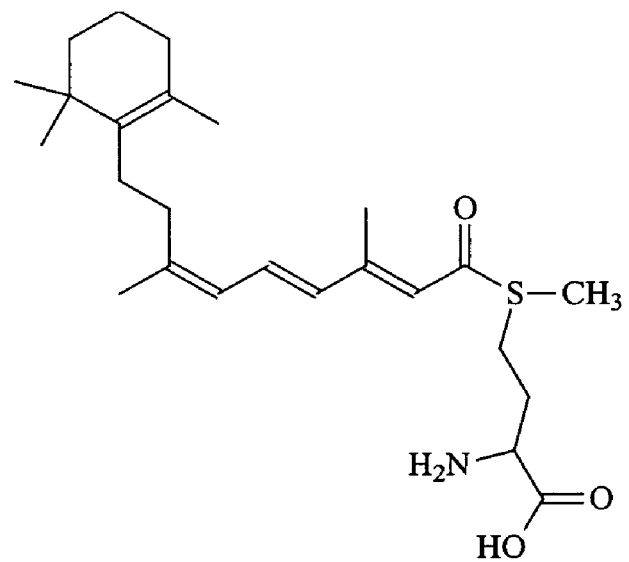

Signal transduction encompasses the temporary interaction of molecules along a cascade, beginning with an upstream trigger molecule, ending at a downstream effector molecule, to elicit a biological response. Biological responses include, but are not limited to, up/downregulation of gene expression, protein synthesis/degradation or posttranslational modification, substrate anabolism or catabolism, changes in subcellular distribution, ion fluxes, triggering of cell death/cell survival. Further descriptions are available in standard textbooks and reviews within the scientific literature. Changes in pathways may physiologically or pathologically occur without detectable and/or lasting alteration of a vital cellular parameter. For instance, phosphorylation of kinases in pathway A may be attenuated, or even counteracted, by an inhibitory parallel event in pathway B; a classical example for this balance between activating and inhibitory pathways is the proliferation control of microvascular endothelial cells (Hanahan and Folkman, Cell 86(3):353-364, 1996) wherein members of the vascular/endothelial growth factor receptor (VEGF receptor) family and members of the tek/tie receptor family execute the activating principle of the pathway control, and transforming growth factor beta receptor (TGFbeta-receptor) executes the inhibitory principle of the pathway control. Another example is differentiation control of early postnatal neurons wherein extracellular bone morphogenetic protein and intracellular SMAD proteins control each other's contribution to neuronal growth and differentiation responses. The majority of signal transduction events reflects a dynamic biochemical balance of signal transduction molecules; only a small subgroup of signal transduction molecules may define a critical cellular parameter (such as proliferation, cell death, expression of a functional specification marker, such as actin and myosin subtypes in muscle cells, synaptic proteins and neurotransmitters in neuronal cells). For a compound to relate to a therapeutically or diagnostically meaningful modulation of a signal transduction pathway, it is a prerequisite that a critical cellular parameter under control of a signal transduction pathway has undergone a detectable and lasting alteration resulting in a pathological cellular imbalance which is to be reported by a diagnostic compound, and to be counteracted by a therapeutic compound.

From a clinical perspective, detectable means that a pathologist and/or a radiologist using state of the art equipment and molecular methodologies will report a pathological readout, and lasting means the pathological readout is present in a time frame of minutes to hours. From a basic science perspective, the relative strength of the alteration would depend on the particular pathway under consideration; in evaluating modulation of gene expression, a reduction by 50% is generally considered efficient, and a reduction by 75% would be scored as close to abrogation of gene expression. It seems reasonable to follow similar standards for the efficiency of signal transduction in general; 50% modulation would be the cumulative alteration of polypeptides participating in a signal transduction cascade resulting in a half-maximal effect at the specified downstream target. It should be noted that in the case of combinatorial modulations at the same target polypeptide, such as posttranslational modification of proteins by phosphorylation or dephosphorylation at several amino acid residues, even lesser degrees of modification at an individual site may exert the cumulative effect of e.g. 25% signal transduction efficiency. It is known from the pharmacological literature that even very small effects in the range of 10% may be statistically significant; such effects should not be excluded, provided statistical significance can be ascertained.

The scope of the invention is on the subgenus of detectable and lasting signal transduction alterations resulting in a pathological cellular imbalance, and their therapeutic reversion or diagnostic reporting by compounds that mimick the geometry and function of cis-configured retinoids.

It is clear from the definitions above that even within the scope of broad and inclusive definitions, neither the terminus modulation nor the biological expression of modulation is indefinite. Further specifications of cell-specific modulation provide additional guidance.

Both examples named above describe cell-specific signal transduction pathways; it is an important principle that cells of different type and lineage, as well as cells of different size, different position, and different activation status, express different signal transduction molecules for the control of functional specification, maintenance and growth. It is known in the art that for example, large cerebellar neurons with highly diversified neurites employ biosynthetic pathways and related signaling molecules distinct from smaller neurons without highly diversified neurites. The ion channel repertoire of an excitable cell is a further distinguishing criterion for cell specificity, and may vary greatly according to the position of the excitable cell within excitable tissue. For example, the rabbit sinus node contains ATP-gated potassium channels at a very high density, whereas surrounding myocardial myocytes express a variety of potassium channels, and lack the regulatory subunit of ATP-gated potassium channels that is characteristic for neuronal cell types. The activation status of a neuron within a developing neural network decides over its survival; a neuron that receives frequent signals will survive and build strong synapses, whereas a neuron that does not receive frequent signals will eventually undergo cell death.

All these examples have in common and delineate that cell-specific signal transduction is connected to a certain pathway within a cell of a certain lineage, size, shape, position, or functional status. The entirety of signal transduction molecules that are predominant in regulating a given signal transduction pathway within a given cell of a certain lineage, or of a certain size, or shape, or position, or functional status comprises the genus of cell-specific signal transduction molecules under the invention.

It is generally believed that retinoids interact in various signal transduction pathways via binding to the retinoid acid receptor (RAR) and/or the retinoid X receptor (RXR) [see e.g., Pfahl et al. *Vitamins and Hormones*, 49, 327-382 (1994)]. For example, binding of retinoids to RAR and/or RXR has been demonstrated in signal transduction pathways involved in apoptosis [see e.g., Kastner, P. et al. The role of nuclear retinoid acid receptors in the regulation of gene expression; Vitamin A in health and disease, Marcel Decker, Inc. New York 189-238 (1994)]. It is further generally believed that the RAR and/or RXR act as nuclear transcription activators as dimers with a further RAR and/or RXR molecule or other nuclear transcription activator.

Surprisingly, Applicant discovered that retinoids and/or retinoid metabolites also bind to cellular polypeptides other than RAR and/or RXR, and other than CRABPI/II, and that binding of the retinoids and/or retinoid metabolites to such cellular polypeptides results in a modulation of the biological effect in signal transduction pathways that functionally include such cellular polypeptides.

Consequently, it is contemplated that a method of cell-specifically interfering with a signal transduction pathway that controls a biological effect in a system may include one step in which the signal transduction pathway is identified as functionally including a cellular polypeptide that binds a retinoid or retinoid metabolite, wherein contemplated cellular polypeptides are polypeptides other than RAR, RXR, CRABPI, CRABPII, and binding of the retinoid or retinoid metabolite to such polypeptides results in a modulation of the biological effect. In a further step, the retinoid or retinoid metabolite is administered to the system in a concentration effective to modulate the biological effect (see detailed description of useful concentrations, infra). The term "binding to a cellular polypeptide" as used herein means that the cellular polypeptide retains a bound substance with a dissociation constant of less than $10^{-3}$/Mol, and specifically excludes binding involved in a catalytic conversion of the retinoid (i.e., binding of a retinoid substrate to an active site of an enzyme that alters the composition of the retinoid). This definition does not exclude binding of a retinoid to a target kinase or phosphatase which does not utilize that retinoid as a substrate.

In one particularly aspect of the inventive subject matter, the inventor discovered that in vivo administration of 9-cis retinoic acid to mice resulted in reduced growth of cardiomyocytes, and specifically lead to apoptosis in cardiac neurons and cells of the cardiac conductance system due to signal amplification in the corresponding mitochondrial signal transduction pathways in the cardiac neurons and cells of the cardiac conductance system (see experimental data, infra).

It should be especially noted, that neuronal cells in general and cells of the cardiac conductance system, as well as cardiomyocytes contain significant amounts of RXR and RAR isofroms [see, e.g., Georgiades P, Brickell P M, Regulation of retinoid X receptor-gamma gene transcript levels in rat heart cells; *Cell Biol Int* 1998; 22(6):457-63, and Kastner et al, Vitamin A deficiency and mutations of RXRalpha, RXRbeta and RARalpha lead to early differentiation of embryonic ventricular cardiomyocytes; *Development* 1997 December; 124(23):4749-58]. If in fact binding of the 9-cis retinoid or its metabolites to the RAR and/or RXR would lead to signal amplification in an apoptosis signal transduction pathway, a person of ordinary skill in the art would expect modulation of the signal transduction pathway in all of the cardiac neurons, cells of the cardiac conductance system, and the cardiomyocytes. However, apoptosis was induced cell-specifically in the cardiac neurons and cells of the cardiac conductance system, but not in cardiomyocytes. The same argument holds for invoking a transcriptional heterodimerization partner NGF1-B/nur77 for RXR which has been proposed to account for retinoid x receptor-mediated apoptosis in certain cancer cell lines (Wu Q et al, Inhibition of trans-retinoic acid-resistant human breast cancer cell growth by retinoid x receptor-selective retinoids, Mol. Cell. Biol. 17, 6598-6608, 1997). NGF1-B/nur77 is known to occur in cardiac myocytes as well as in neuronal and neuroendocrine cells. Therefore, it is contemplated that modulation of the apoptosis signal transduction pathway is not primarily mediated by binding of the 9-cis retinoid to the RAR and/or RXR, or to a heterodimeric form of RXR, but by binding of the 9-cis retinoid to an alternative binding target.

ATP-gated Potassium Channel (KATP):

With respect to the alternative (non-RAR/non-RXR/non-CRABP) binding target of 9-cis retinoid or its metabolite, it should be appreciated that cardiac neurons, cells of the cardiac conductance system, and cardiomyocytes are known to have functional ATP-gated potassium channels (KATP), which is a specific form of a ligand-gated inward rectifier potassium channel (Light P E et al. Cardiovascular Res. 44, 356-369, 1999). ATP-gated $K^+$ channels on the cell surface are the most critical ion channel activity during the repolarisation phase, i.e. the return of previously excited neuronal membranes or cardiomyocyte membranes to the excitable ground state. In cells belonging to the cardiac pacemaker system, also described as cells of the cardiac conductance system (i.e. sino-atrial node, atrioventricular node, and Purkinje fibers), KATP plays a fundamental role in coordinating cardiac excitability. The ionic components of cardiac pacemaking have been reviewed in Irisawa H et al., Cardiac pacemaking in the sino-atrial node, Physiol. Rev. 73, 197-227, 1993.

It is further known (Xu B. et al., Induction of human myeloblastic ML-1 cell G1 arrest by suppression of K+ channel activity, Am. J. Physiol. 271 (Cell Physiol. 40):C2037-2044, 1996; Dubois J. M. and B. Rouzaire-Dubois, Role of potassium channels in mitogenesis, Progr. Biophys. Mol. Biol. 59, 1-21, 1993; Glia 30, 39-48, 2000) that inward rectifier potassium channels in general play an important role in cellular proliferation and cell cycle progression (the latter is an obligatory event for the successful execution of the cellular apoptosis program). A specific role for KATP in cellular proliferation control, beyond a role as facilitator of Ca2+ signaling, has been described (Malhi H et al., KATP channels regulate mitogenically induced proliferation in primary rat hepatocytes and human liver cell lines, J. Biol. Chem. 275, 26050-7, 2000). Cell-surface KATP can participate in potentially pro-apoptotic pathways through an indirect electrical effect: plasma membrane depolarization triggered by KATP block can activate voltage-gated Ca-channels which generate Ca2+ fluxes from the outside into the cytoplasm (Gribble F et al., The essential role of the Walker A motifs on SUR1 in K-ATP channel activation by Mg-ADP and diazoxide, EMBO J. 16(60), 1145-1152, 1997).

Besides containing KATP channels that are expressed on the cellular surface, many cell types, including cardiac myocytes, neurons and pacemaker cells, also contain functional KATP channels in their mitochondria. The molecular composition of mitochondrial KATP is less certain, and it is possible (and contemplated) that alternative regulatory subunits participate in its composition and functional control. There is no firm evidence so far that mitochondrial KATP modulates the irreversible transition of mitochondrial potential that precedes apoptotic cell death (Balakirov M Y and Zimmer L, Gradual changes in permeability of inner mitochondrial membrane precede the mitochondrial permeability transition, Arch. Biochem. Biophys. 356, 46-56, 1998), although it is contemplated that cross-talk exists between regulatory pathways of mitochondrial KATP and regulatory pathways of the mitochondrial pro/antiapoptotic proteins of the bcl family.

ATP-gated $K^+$ channels expressed on the cellular surface function as an octameric protein complex of 4:4 stoichiometry between inward rectifying potassium channel molecules of the Kir 6.x class and sulfonylurea receptor (SUR) molecules (reviewed in Aguilar-Bryan L and Bryan J, molecular biology of adenosinetriphosphate sensitive potassium channels, Endocr. Review 20, 101-135, 1999). In comparison to the complex of Kir 6.1 with the isoform SUR2 that is expressed on cardiomyocytes, the complex of Kir 6.1 with the SUR isoform SUR1 (expressed on neuronal and neuroendocrine cells) displays markedly distinct ATP-binding kinetics and allosteric regulation. An even more pronounced difference between SUR1 and SUR2 is detectable with regard to sulfonylurea binding; the affinity constant for sulfonylurea drug binding to SUR1 is an order of magnitude higher than the affinity constant for sulfonylurea drug binding to SUR2. Due to these characteristics, small pharmacological molecules can participate at multiple binding sites in multiple binding equilibria that differentially regulate SUR isoform function. It is further known that binding of various substrates besides and beyond MgADP, ATP, GTP, GDP, ITP, PIP, PIP2 to SUR1-Kir 6.x complexes modulates the activity of ATP-gated $K^+$ channels (Baukrowitz T et al. PIP2 and PIP as determinants for ATP inhibition of KATP channels, Science 282, 1141-1144, 1998; Fan Z and Makielski J C, Anionic phospholipids activate ATP-sensitive potassium channels, J. Biol. Chem 272, 5388-5395, 1997; Heron L et al., Human alpha-endosulfine, a possible regulator of sulfonylurea-sensitive KATP channel: molecular cloning, expression and biological properties, Proc. Natl. Acad. Sci. U.S.A. 95, 8387-8391, 1998; Holemans et al., Interaction of fluorescein derivatives with glibenclamide binding sites in rat brain, Neuroscience Lett. 183, 183-186, 1995]. Also, KATP is subject to direct regulation of ion channels by fatty acids (Garlid KD, Cation transport in mitochondria—the potassium cycle, Biochim. Biophys. Acta 1275, 123-126, 1996; a broader review on this topic is found at Ordway R W et al, Direct regulation of ion channels by fatty acids, Trends in Neuroscience 14, 96-100, 1991). Based on observations of the inventor (unpublished data), but not whishing to be bound to a particular hypothesis or theory, it is contemplated that retinoids and their metabolites, particularly those adopting 9cis-configuration, specifically and differentially bind to SUR isoforms and/or the SUR-$K^+$ channel complex including regulatory G-proteins. It is further contemplated that such binding modulates the activity of the ATP-gated $K^+$ channel; whether the binding of a cis-configured retinoid results in activation or block of the KATP, may depend on the exact structure of the retinoid and on the cellular context (binding to surface KATP vs. binding to the mitochondrial KATP, binding to KATP in cells that are close to homeostasis vs. cells that are metabolically stressed or hypoxic, binding to KATP in cells wherein KATP is structurally and/or functionally linked to large superstructures, including but not limited to gap junctions formed by connexins). It is highly desirable to have the option for either block or activation in the design of therapeutically useful retinoids.

With regard to the potential binding site of the retinoid/retinoid metabolite and its competition with known regulators of SUR1, it must be appreciated that GTP binding sites can differ markedly in sequence and in structure from ATP binding sites (reviewed in Muller G, Towards 3D structures of G protein-coupled receptors: a multidisciplinary approach, Curr. Med. Chem. 7, 861-888, 2000), such that prediction of ATP binding to a chosen site does not imply GTP binding, or GDP binding, to that site. Likewise, 9cis-RA binding sites and all-trans-RA binding sites are different in sequence, structure and function, such that knowledge or prediction of an all-trans-RA binding site putatively overlapping with an ATP binding site does not provide knowledge of and ability to predict a 9cis-RA binding site putatively overlapping with an ITP (IDP) binding site, a PIP (PIP2) binding site, or a GTP (GDP) binding site. Furthermore, from pharmacological experiments, it is known that e.g. lipid fluorescein derivatives compete with sulfonylurea for binding to the—yet poorly defined—sulfonylurea binding site(s) on SUR1 which are not identical with the rather well-defined nucleotide binding sites (Schwanstecher et al., Interaction of fluorescein derivatives with sulfonylurea binding in insulin-secreting cells, Pharmacology 50, 182-191, 1995; Holemans et al, ibid.).

Previously, Kitabayashi et al. (in: In Vitro Cell. Dev. Biol. 30A:761-768, 1994) have suggested that within the context of in-vitro differentiation, all-trans retinoic acid may have functions beyond the activation of the well-established transcription factors RARalpha, beta, gamma. One versed in the art will appreciate the paradigm of stereoselective retinoid function, namely that stereoisomers of the cis vs. trans series bind to distinct proteins: all-trans retinoic acid binds to RAR with high affinity (see for example, Graupner et al., Biochem. Biophys. Res. Comm. 179(3):1554-1561, 1991), but not significantly to RXR which, conversely, binds 9-cis-retinoic acid with high affinity. In full agreement with said paradigm, the modulatory effects on signal transduction under the invention depend on cis-configuration of the retinoid, and cannot be achieved to any significant degree by employing all-trans retinoic acid, thus Kitabayashi et al. cannot practice and cannot anticipate the method under the invention by employing all-trans-retinoic acid. Furthermore, P19 cells used by Kitabayashi et al. differentiate into neuronal cells which, when exposed in vivo to cis-configured retinoic acid or retinoids, would be particularly susceptible to programmed cell death under the method of the invention; however, Kitabayashi et al. disclose morphological changes during cell differentiation but not appreciable cell death in their in vitro system. Again, one versed in the art would appreciate that retinoid metabolites considered important under the invention would differ substantially between in vitro and in vivo systems. Therefore, it is to be anticipated that the target molecules of Kitabayashi's method are distinct from the target molecules under the invention. (Applicant has performed further experiments to distinguish the pre-natal repertoire of signal transduction which may be more similar to the system investigated by Kitabayashi et al. from the perinatal/early postnatal repertoire of signal transduction in mouse heart that is the basis for the disclosure under the invention).

Figure 2:
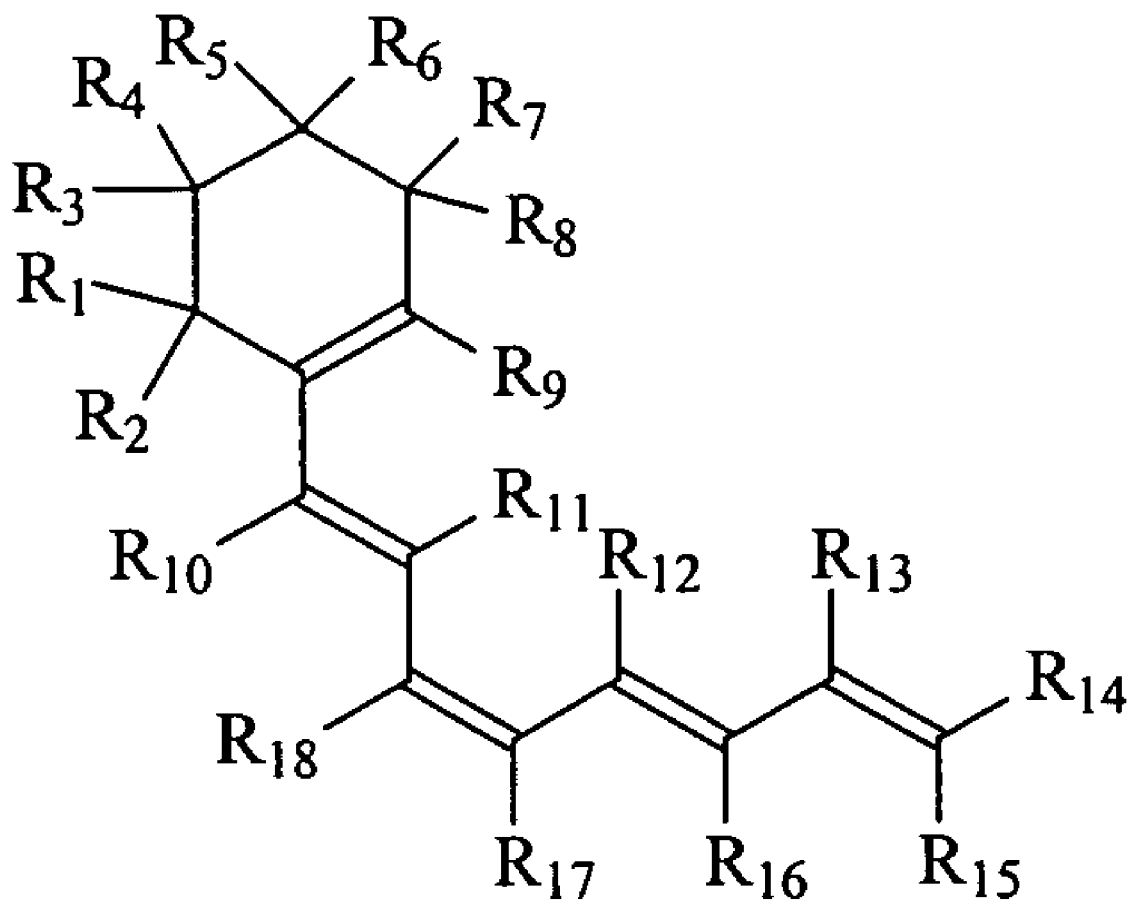
FIG. 2 depicts further exemplary structures of retinoids and retinoid metabolites.
Figure 3A:
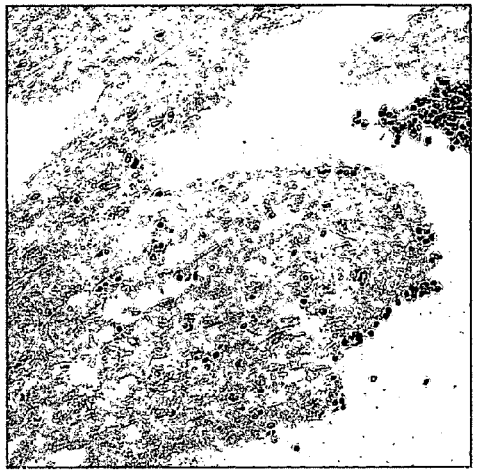
FIG. 3A-3D are a set of confocal laser micrographs, depicting colocalization of apoptosis in cardiac conductance cells of a perinatal mouse heart after administration of 20 mg/kg 9cis-RA, vs. absence of apoptosis in cardiac conductance cells of a perinatal mouse heart after administration of carrier.
Figure 3B:
Figure 3C:
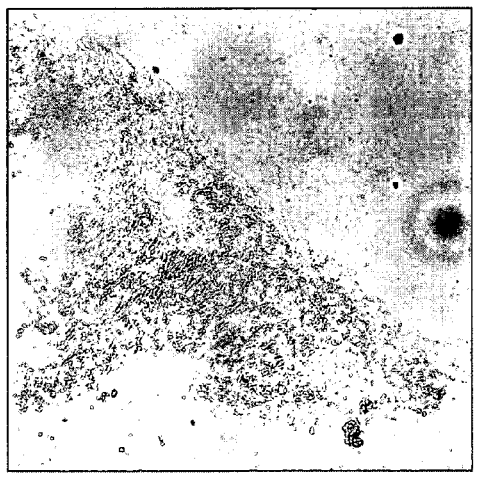
Figure 3D:
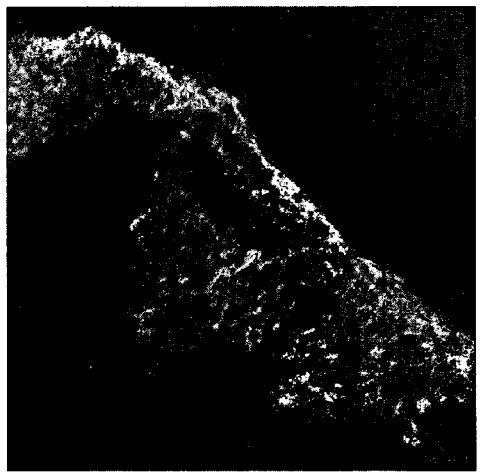
Figure 4A:
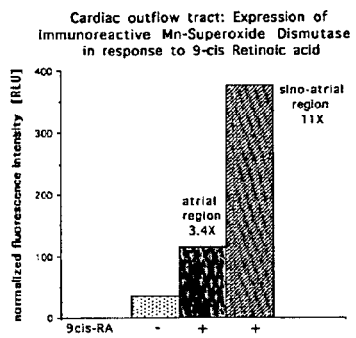
FIG. 4A-4D are graphs depicting the upregulation of immunoreactive Mn-dependent Superoxide Dismutase (Mn-SOD) in mitochondria of cells in the cardiac outflow tract after administration of 20 mg/kg 9cis-RA as fold induction of the corresponding control signal after administration of carrier.
Figure 4B:
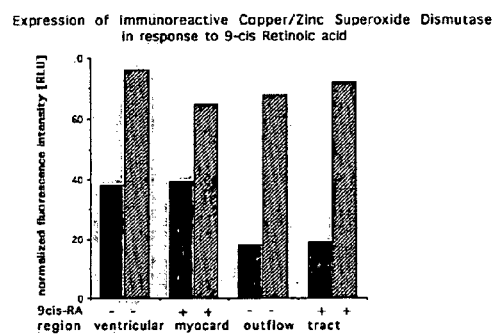
Figure 4C:
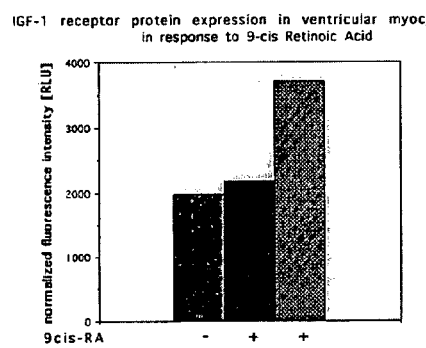
Figure 4D:
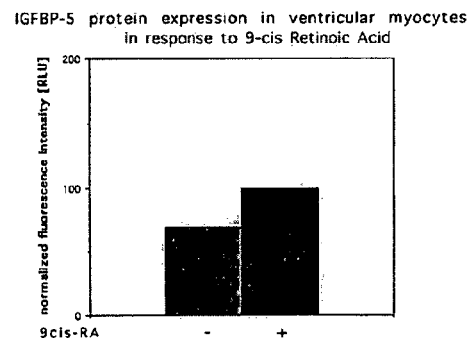

As further distinguishing aspects between the method of Kitabayashi et al. and the method under the invention, it is established that differentiation of precursor cells by all-trans retinoic acid involves activation of transcription factors of the RAR series. The observations of Kitabayashi represent a combination of conventional transcription factor activation (likely to be the dominating effect) with signal transduction effects (the phosphoprotein patterns are scored 14 h after the onset of RARbeta induction; FIG. 5 and FIG. 2 demonstrate that F9 differentiation may be achieved in the absence of any exogenous all-trans-retinoic acid, and the combined effect of all-trans retinoic acid and protein kinase inhibitor staurosporine is moderately larger than the effect of staurosporine alone). The method disclosed by Kitabayashi et al. does not permit to activate signal transduction without simultaneously activating transcription factors of the RAR series. In contrast, the method under the invention explicitly excludes interaction with a transcription factor of the RAR or RXR series as a significant mode of action.

The leading argument of Kitabayashi et al. is the induction of the jun promoter in absence of RARbeta protein induction which effect is suggested to reflect nuclear receptor-independent induction of differentiation through retinoic acid. Jun is an immediate-early gene that is activated in a large variety of cell types under a large variety of conditions; thus jun expression is not a cell-specific signal transduction response as defined under the invention. It is well established that in a variety of promoter contexts, all-trans retinoic acid-activated RAR inhibits jun activity in the form of the jun/fos heterodimer. Even if the initiation of jun expression would be considered independent of RAR, jun in the form of jun/fos heterodimers would be inhibited and could not initiate differentiation of F9 and P19 cells. Furthermore, Applicant has participated in research (published prior to the disclosure by Kitabayashi) teaching that at least in vitro, all-trans retinoic acid-activated RAR may directly interact with the jun protein, and teaching further that jun-RAR complexes may exist in vivo. Thus, it may be anticipated that a jun-RAR complex may participate in regulating the differentiation of F9 and P19 cells; again in a different aspect, such a nuclear receptor-containing complex would not be consistent with the suggestion of nuclear receptor-independent transactivation.

Kitabayashi et al. do not appear to consider that RARalpha is typically present in virtually all mammalian cell types at low levels, and may be the pre-existing factor mentioned on p. 766, right column, line 55. RARalpha may be inducible by very low concentrations of all-trans-retinoic acid, starting a cascade of jun induction and subsequently RARbeta induction. The technical specifications by Kitabayashi et al. do not comprise rigorous data about the absence of RARalpha and RARbeta during the critical stage of onset of differentiation under their experimental conditions (no control experiments in the presence of RARalpha antisense and RARbeta antisense constructs, no control experiments in the presence of inhibitory RAR ligands), leaving the conclusions about nuclear receptor-independent effects of all-trans retinoic acid inferential. Further limiting is the use of the teratocarcinoma cell lines F9 and P19. Both cell lines do not represent authentic stem cells, and for the use of retinoids in authentic stem cells, no retinoid functions other than nuclear receptor-mediated functions are taught in the art.

In summary, one versed in the art would conclude that the method under the invention is distinct from the method disclosed by Kitabayashi et al. in several aspects, teaches away from the observations and disclosure of Kitabayashi et al., and cannot be anticipated based on the disclosure by Kitabayashi et al.

Retinoids:

With respect to the retinoid, it is contemplated that all known retinoids are suitable for use in conjunction with the teachings presented herein, and exemplary retinoids are described in Chemistry and Biology of Synthetic Retinoids (Marcia Dawson, William H. Okamura (Editor), CRC Pr; ISBN: 0849347971), Retinoids: The Biochemical and Molecular Basis of Vitamin A and Retinoid Action (Heinz Nau (Editor), William S. Blaner (Editor); Springer Verlag; ISBN: 3540658920), or Retinoids (Maria A. Livrea, Lester Packer (Editor); Marcel Dekker; ISBN: 0824787587), all of which are incorporated by reference herein. However, it is preferred that the retinoid comprises at least one cis-configuration, and it is particularly contemplated that the cis-configuration is a 9-cis configuration (e.g., 9-cis retinoic acid). Exemplary retinoids are depicted in FIG. 2, in which $R_1$-$R_{18}$ are independently selected from H, Halogen, alkyl, alkenyl, alkynyl, aryl, alkraryl, all of which may independently further comprise a halogen, a functional group (e.g., a CHO, COOH, $NO_2$, NO, $NH_2$, NH, $SO_2$, SO, $PO_4^{3-}$), a polar and/or hydrophilic group, including mono-, di-, and polysaccharides, a non-polar and/or hydrophobic group, including fatty acids, lipids, steroids, etc, and an amino acids and/or an amino acid derivatives. Contemplated $R_1$-$R_{18}$ may further comprise heteroatoms, which may be in various positions of $R_1$-$R_{18}$, including pending or in the backbone. Where stereoisomeric or chiral variations of contemplated retinoids exist, all chemically reasonable configurations (of R, S, cis, and trans) are contemplated. For example, suitable retinoids need not be limited to the depicted 9-cis configuration, but may also include all-trans, 9-cis-11-cis-13-trans configuration, etc. However, the term "retinoid" as used herein particularly excludes retro-retinoids as described in "Retro-Retinoids in Regulated Cell Growth and Death, O'Connel et al., J. Exp. Med. 184: 549-555, 1996).

In further contemplated aspects, retinoid analogs are contemplated suitable alternative retinoids. The term "retinoid analog" as used herein refers to any molecule that displays an activity conventionally ascribed to retinoic acid derivatives as summarized in U.S. Pat. No. 6,034,242 to Vuligonda et al. (Mar. 7, 2000), which is incorporated by reference herein. An especially contemplated retinoid analog is 4-hydroxyphenyl-retinamide or a 4hydroxyphenyl-retinamide analog, as described in U.S. Pat. No. 6,117,845, which is also incorporated by reference herein. Further contemplated retinoid analogs especially include known bicyclical spaced conformationally constrained ligands of RXR, and particularly include RXR agonists such as LG1069, and compounds described by Benoit G et al (RAR-independent RXR signaling induces t(15;17) leukemia cell maturation, EMBO J (1999) 18(24), 7011-7018).

It should be particularly appreciated that the retinoid or retinoid analog may also be metabolized in one or more biochemical (e.g., enzymatic) or thermodynamical (e.g. thermal isomerization) conversion to form a retinoid metabolite or retinoid analog metabolite. There are numerous metabolic conversions in which the retinoid and/or retinoid analog may be metabolized, and all of the known metabolic conversions are contemplated. For example, a metabolic conversion may include addition of a chemical function or group, including polar, charged, lipophilic or hydrophilic groups, sulfur, nitrogen, or oxygen containing groups, etc. Further contemplated groups particularly include sulfates, thiols, and adenosyl methionine., pentoses, hexoses, heterocyclic natural compounds linke to sugars or alkohols. Consequently, it is contemplated that retinoid metabolites include a sulfated retinoid and S-adenosylretinoid, and stereoisomeric forms of retinoyl-inositides.

It is established for 9cis-RA and synthetic receptor-selective retinoids that in concentrations of $10^{-9\,M}$, $10^{-8}$ M or $10^{-7}$ M, transcription factor activation is achieved; $10^{-7}$ M, better $10^{-6}$ M and $10^{-5}$ M is required for F9 cell and P19 cell differentiation when using certain synthetic receptor-selective retinoids (Applicant's observation); the observations under the invention comprise a growth-inhibitory effect at 10 mg/kg (i.e. an effect of interfering with a growth factor-dependent pathway), and a pro-apoptotic effect at 40 mg/kg. More pronounced at concentrations of $10^{-3}$ M and above, direct toxic effects on membranes may be observed for retinoic acids regardless of stereoisomeric form.

For the modulation of signal transduction under the invention, the low micromolar range would be considered the typical concentration range; however, it is within the full scope of the invention to use methods of combinatorial chemistry to obtain compounds with high selectivity for a signal transduction target, and biological activity in vivo in the nanomolar range.

Applicant has conducted further experiments with synthetic retinoids that fall into two categories: synthetic retinoids of the RXR-selective type at 10 mg/kg have limited efficacy in vivo in reduction of mouse heart size and weight in the perinatal mouse heart model (up to 20% of 9cis-RA), whereas synthetic retinoids without RXR selectivity at 10 mg/kg show increased efficacy in vivo (50% of 9cis-RA and more). Furthermore, synthetic retinoids of the RXR-selective type did not induce apoptosis at 40 mg/kg. These results provide clear guidance towards the structure of synthetic retinoids that may be particularly suitable for the modulation of signal transduction under the invention.

Such retinoids are without the rigidity of backbone-stabilizing ring systems used in RXR-selective compounds; they are stably cis-configured and provide flexibility of the aliphatic side chain, but not the full degrees of rotational freedom encountered in 9cis-RA. These are the structural characteristics common among the different species of retinoids disclosed and contemplated for modulation of signal transduction. It is further contemplated that this subgenus of retinoids will represent the prototype for the design of combinatorial libraries to discover novel later-generation retinomimetic signal transduction modifiers (RMSTM).

Observations from testing RXR-selective compounds in vivo indicated that the backbone-stabilized rigid ring systems cause considerable toxicity; it is therefore contemplated that relaxed rigidity will provide efficacy at substantially reduced toxicity. Multiple procedures exist in synthetic Organic Chemistry to relax the rigidity and planarity of ring systems; a classical way is the introduction of heteroatoms into the common bonds shared between adjacent ring systems, leading to angles between the planes defined by the individual rings; another the introduction of heteroatoms into positions that are not shared; this may lead to abrogation of strict planarity within a given ring, under maintenance of the geometry of the connection to an adjacent ring. The introduction of heteroatoms carrying free electron pairs (as in oxygen and nitrogen) also changes the local solvation properties of the modified ring system, favoring more hydrophilic interactions (which may alter the selectivity for binding partners among signal transductin molecules). Another way is the substitution of carbon-based ring systems by short peptidomimetic building blocks derived from alanin or glycin. Further guidance for the structural diversity contemplated is provided by FIG. 2.

Based upon what Applicant has investigated in the area of retinoids and channel interaction, it would be expected that signal transduction molecules other than channels with similar binding sites for allosteric molecules or small molecule ligands may interact with retinoids. In a highly preferred embodiment of the invention, the beta-ionone ring of a retinoid is expanded in its dimensions to make it resemble more closely the ring systems found in inositol and adenosin. This modification allows for better competition of the modified retinoid with endogenous inositol derivatives and adenosin derivatives for the binding site on inositol receptors, inositol transporters, and inositol-metabolizing enzymes, or on adenosine receptors, adenosin transporters, and adenosine-metabolizing enzymes, and on kinases and phosphatases.

The summary of the structural, functional, physical, and synthetic characteristics enables one skilled in the art to identify which retinoid falls within the scope of the invention and the claimed subgenus of retinoids.

Retinoids may modulate signal transduction in a variety of ways:
    by competition with small molecule phosphorylated nucleotide messengers (charged lipids, phytic acid, hydroxynonenal) binding to specific domains on signal transduction molecules (preferentially kinases, phosphatases, nucleotide receptors); (example: binding to nucleotide-binding domain 1 in SUR1 or SUR2A)

by acting as allosteric modifier, binding to regulatory sequences that are not part of a second messenger binding region, and that trigger conformational changes activating or interrupting signal transduction;

by altering the lipid environment surrounding membrane proteins locally, thus altering enzymatic specificity and/or substrate affinity for kinases or phosphatases, or altering ligand affinity and/or ligand specificity for receptors (example: membrane perturbations typically require high concentrations in the low millimolar range which are quite toxic);

by blocking metabolism of either signal transduction molecules or pharmacological agents (example: targeting members of the glutathion-S-transferase (GST) family will reduce metabolism and catabolism of a wide range of GST substrates, depending on the individual GST isoform inhibited most efficiently; GST substrates include hormones, toxic exogenous compounds, pharmaceutical drugs;

by exerting pro-apoptotic activities, preferably in tumor cells, through mitochondrial molecules such as transporters (example: activating ANT and thus triggering programmed cell death).

For the specific interaction of cis-configured retinoids with polypeptides under the invention, only limited guidance is available, e.g. provided by the crystallographic analysis of the five-stranded coiled-coil domain of the cartilage oligomeric matrix protein (Guo et al., EMBO Journal 18:5265-5272, 1998); this protein, in its axial pore, may bind a variety of hydrophobic substances, including benzene, vitamin D, and all-trans-configured retinol and all-trans-configured retinoic acid which is not a structure selectable under the invention. Except for the hydrogen bonding of the hydroxyl group at the end of the isopren side chain to Gln54, the overall nature of all-trans-retinol binding to the pore of is described as hydrophobic, with the beta-ionone ring located in the cavity between the Thr40 and Leu44 side chains whereby the C16, C17 and C18 methyl groups of the beta-ionone ring are in van der Waals contact with the C-delta and C-epsilon side chain atoms of Leu44.

A certain amount of specific guidance is further provided by analysis of chimeric SUR receptors constructed from divergent regions found in individual SUR isoforms. In SUR2A, the transmembrane domains 12-17, next to the nucleotide binding domain 2 near the C-terminus, confer binding to the channel opener cromakalim (D'Hahan et al., Mol. Pharmacol. 56:308-315, 1999), whereas the nucleotide-binding domains are indispensable for binding of the channel opener diazoxide (Gribble et al., EMBO J. 16:1145-1152, 1997); diazoxide does not have a contiguous binding site. Binding sites for channel openers may encompass the ATP binding site, preferably the first nucleotide-binding region (NBD1), known as the high-affinity site for ATP binding in SUR1. Alternatively, binding sites for channel openers may be mostly formed by structures outside of the nucleotide-binding regions; in analogy to regulatory binding sites in bacterial ATP binding cassette proteins, such binding sites would preferably constitute the SUR portion spanning between transmembrane domain 17 and the second nucleotide-binding domain.

It is a preferred mode of the invention to utilize the highly malleable basic structure and amphipatic characteristics of retinoids (lipophilic side chain, together with a terminal charge and a flexible ring system) (see FIG. 2) to engineer small molecules of unique structural flexibility for selective interaction with signal transduction molecules in silico, and to map retinoid derivatives to interaction sites based on established principles in structure-based modeling. Existing databases of protein sequences (such as those available through the web site of the National Center of Biotechnology Information at www.ncbi.nlm.nih.gov) and protein structures (e.g. the Brookhaven Protein Database) provide further guidance to the systematic analysis of potential interaction sites. Much of the initial identification may be performed without any experimentation, by querying databases.

Since the crystal structure of the ligand binding site in RXR is known, detailed structural information is available to define structure-activity-relationships (SAR) that are not desirable and need to be excluded to practice the art under the invention. Different software packages for structural simulation and docking of ligands to proteins are known in the art and have been made commercially available, such that a person versed in the art could, by docking of a candidate retinoid structure to the RXR ligand binding domain, recognize and exclude retinoid structures that are to be excluded under the invention. By choosing a candidate protein from the subgenus of signal transduction proteins that has undergone a detectable and lasting alteration resulting in a pathological cellular imbalance, and docking a candidate retinoid structure onto said candidate protein, a person versed in the art could recognize a suitable retinoid and perform a positive selection of a retinoid modulating a signal transduction pathway under the invention. Neither negative selection nor positive selection would require any experimentation at all; computer-assisted structural simulations are acknowledged as standard in the art.

Formal proof in possible in tissue culture models (mammalian), wherein RAR expression, RXR expression, and cellular retinol-binding protein is under control of an inducible knockout mechanism (multiple systems are known in the art, some of them commercially available); upon addition of inducer to culture medium, RXR is downregulated without affecting cell viability for the duration of the screening experiment. The desired biological effect may be validated in the absence of RXR, and the absence of RXR validated in a PCR experiment at the end of the screening experiment. *Spodoptera frugiperda* cells (insect cells established as host for commercially available baculovirus protein expression systems) or yeast strains do not naturally contain the full content of RAR, RXR, and cellular retinol binding protein that is found in mammalian cells, but have many signal transduction pathways in common with mammalian cells.

A simplified screening procedure for retinoids—which is the most highly preferred embodiment of a testing system for compounds under the invention—would engage yeast strains engineered to overexpress one component or several components of a desired signal transduction pathway; it is known in the art that yeast strains do not express endogenous RAR or RXR (Hall et al., Proc. Natl. Acad. Sci. USA 90:6929-6933, 1993) such that retinoid effects on signal transduction molecules results from yeast models can be scored and interpreted directly without the confounding effect of nuclear receptor activity. *Spodoptera* cells would require only one genetic engineering step, namely the insertion of an inducible knockout of the ultraspiracle gene (the insect homologue of RXR). Such engineered systems are amenable to high-throughput screening of thousands of retinoid candidate molecules, if so desirable. Engineered cellular systems are commonplace in contemporary drug discovery settings and do not represent examples of undue experimentation. Such screening procedures may be performed on single compounds after structural simulation in silico, or after initial selection of a candidate structure to be derivatized in a combinatorial library guided by structural simulations, or (least preferred)

as part of a discovery program that starts out with a minimum of structural constraints and processes a maximum of synthesized compounds.

A system useful for detecting, quantifying and validating retinoid-mediated interference with signal transduction under the invention would be operative with commercially available technology for gene knockdown (either as inducible knockout, or utilizing a small inhibitory RNA).

One of the highly preferred applications of retinoids under the invention is to design improved potassium channel openers. Current potassium channel openers are limited by their poor tissue selectivity (i.e. no distinction between cardiac and non-cardiac potassium channels) and their low affinity. There is a pharmacological need to design and develop novel molecules that demonstrate cell-selective modulation of potassium channels or regulatory subunits of potassium channels at high affinity. For purposes of providing a useful pharmacological agent, induction of apoptosis in sinus node cells or cardiac myocytes is generally undesirable. Stunting of myocardial growth may be clinically useful in patients suffering from hypertrophic cardiomyopathy, a genetically diverse and mostly fatal condition wherein the functional myocard is destroyed by excessive growth. Instead, it is higly desirable to elicit cardioprotective properties by generating derivatives of retinoids that act as cardioselective channel openers on SUR2A.

Channels Other than KATP:

Potassium channels have also been linked to learning and memory. One of the earlier observations in the pathophysiological dissection of Alzheimer's disease was the discovery of altered potassium channel function. In general, potassium channel openers are not favorable for learning and memory in the context of behavioral studies, but the effect depends on the potassium channel subtype. Mice with disabled Kv channel subunits have been studied as a model for mild learning and memory deficits. Small conductance $Ca^{2+}$ activated potassium channels dampen excitability through a phenomenon called afterhyperpolarizations (Nicholl, Science 241:545-551, 1988); reducing the activity of these channels is contemplated as beneficial to improve learning and cognitive impairment. Cognitive enhancers like piracetam reduce activity of slow-inactivating potassium channels, such as IDR and IK(Ca), while maintaining or activating fast-inactivating potassium currents.

While a complex process such as learning is characterized by many functional components and neuroanatomical localizations, a cerebellar component has been consistently observed. The block of a voltage-dependent transient outward potassium flux through serotonin was found to increase cerebellar Purkinje cell activity (Wang Y et al., Brain Res. 571(2):345-349, 1992) which would be favorable for learning and enhanced mood. The selective serotonin reuptake inhibitor fluoxetine (Prozac™) inhibits potassium channels in a cell type-specific manner; apparently, different types and isoforms of potassium channels couple to the serotonine transporter in different cell types. Thus, modulating the activity of potassium channel isoforms coupling to serotonin transporters and/or serotonin receptors would be a pharmacological tool to improve mood and to treat different forms of depression.

Diseases linked to impaired potassium channel function are well documented (see for example Cooper and Jan, Proc. Natl. Acad Sci. USA 96:4759-4766, 1999); the channel hKCa3 from the family of small conductance $Ca^{2+}$-activated potassium channels has been implicated as a risk factor for mood disorders and schizoaffective disorders in Caucasian populations (see Li et al., Biochem. Biophys. Res. Comm 251:662-665, 1998).

Sigma receptors are known to form complexes with potassium channels in the membrane of the endoplasmatic reticulum, and to functionally cooperate with inositol-trisphosphate signal transduction, through modulation of $IP_3$-receptors and $Ca^{2+}$ signaling. Within these complexes, sigma receptors are believed to serve as signal transduction enhancer for effects mediated through other binding partners. Thus, potassium channel modulation could affect $IP_3$ receptor function and vice versa. As sigma receptors contribute to learning and memory functions, pain perception, and psychostimulant-mediated behavior (cocain in particular), potassium channel modulation and/or $IP_3$ receptor modulation are contemplated to improve learning and memory, and to reduce pain perception and addictive behavior.

Certain potassium channel openers, including the KATP opener cromakalim, were found to increase the immobility time in the forced swim test which serves a surrogate marker for clinical depression in rodents. Abrogation of the Kv1.1 gene expression by antisense treatment in vivo increased immobility time as well (Galeotti et al., Br. J. Pharmacol. 126(7):1653-9, 1999). Thus selective potassium channel opening of the Kv1 subtype, preferably combined with selective KATP blockage, by retinoids is contemplated to be a beneficial treatment for clinical depression in patients.

It should still further be appreciated, that the cellular polypeptide to which the retinoid or retinoid metabolite binds need not be restricted to an ATP gated $K^+$ channel complex or a different type of potassium channel complex, and alternative polypeptides include ion channels with a selectivity for calcium ions or sodium ions, or chlorine ions (CFTR). Functional cooperation of an alternative ion channel with an alternative regulatory polypeptide may be exemplified by the complex comprising an inward rectifier potassium channel HERG with a member of the MinK family of regulatory transmembrane peptides (Sanguinetti et al., Coassembly of K(V)Lqt1 and MinK (Isk) proteins to form cardiac I-Ks potassium channel, Nature 384, 80-83; Abbott G W et al., MiRP1 forms Ikr potassium channels with HERG and is associated with cardiac arrhythmia, Cell 97, 175-187, 1999). It is especially contemplated that the ion channel functionally cooperates with a regulatory polypeptide, such as SUR. The term "ion channel functionally cooperates with a SUR" as used herein means that the activity of the ion channel is directly or indirectly influenced by the SUR. The term "directly influenced" as used herein means that the SUR is physically coupled to the ion channel, and that binding of the retinoid to the SUR and/or SUR-ion channel complex influences the activity of the ion channel. The term "indirectly influenced" as used herein means that the SUR is not physically coupled to the ion channel, and that the activity of the ion channel may be modulated by at least one intermediary molecule between the SUR and the ion channel complex when the retinoid or retinoid metabolite binds to the SUR.

Consequently, it is contemplated that alternative biological effects (i.e., biological effects other than apoptosis) include all biological effects that are mediated by a signal transduction pathway, which includes an ion channel and/or an SUR. For example, it is known that insulin secretion of neuroendocrine cells is at least partly regulated by the activity of a $K^+$ ion channel and/or SUR1 [Gribble F et al. Tissue specificity of sulfonylureas, Diabetes 47, 1412-1418]. Similarly, various neuroendocrine disorders that are at least partly linked to activity of a $K^+$ ion channel and/or SUR are contemplated. Furthermore contemplated diseases include cystic fibrosis, which is known to involve malfunction of a chloride ion channel (also a member of the ABC protein family) in the pathogenesis. In another example, contemplated biological effects may also include cell growth, cell division, and arrythmia, all of which are contemplated to be modulated by a signal transduction pathway that includes an ion channel and/or SUR [Malhi H et al, ibid.; Noble D, The ionic basis of the heartbeat and of cardiac arrhythmias, in: B N Singh, H J J Wellens, M Hiraoka (eds): Electropharmacological Control of Cardiac Arrhythmias, Mount Kisco, N.Y., Futura Publ. 1994, p. 3-20, and following chapters].

A further highly preferred target for cell-selective modulation of signal transduction by cis-configured retinoids is the mitochondrial permeability pore system, combining the channel elements VDAC (across the outer mitochondrial membrane; Colombini, Nature 279:643-645, 1979) and adenine nucleotide transporter ANT (transport across the inner mitochondrial membrane). VDAC constitues a major pathway by which metabolites such as ATP/ADP or succinate, can be exchanged between the cytosol and the mitochondrion (reviewed in Benz, Biochim. Biophys. Acta 1197: 167-196, 1994); Lawen et al. (in: Protoplasma 205:10-20, 1998) also teach that VDAC may be linked to apoptosis. ANT is part of a large oligomeric complex displaying properties of the permeability transition pore PTP (Beutner et al., Biochim Biophys Acta 1368(1):7-18, 1998). PTP maintains the mitochondrial membrane potential and is the molecular substrate for the commitment to programmed cell death due to stable loss of membrane potential; activation of PTP causes cell death. Cell survival proteins, such as bcl-2 (Marzio et al., Science 281:2027-2031, 1998) or the viral mitochondrial inhibitor of apoptosis (Goldmann et al., Proc. Natl. Acad. Sci USA 96:12536-12541, 1999), interact with ANT. The pharmacological response of PTP is cell-specific. In liver mitochondria, tamoxifen blocks calcium-induced PTP activation, and acts cytoprotective (Custodio et al., Biochem. Pharmacol. 47(11), 1989-1998, 1998). In neuronal mitochondria, tamoxifen induces apoptosis at high concentrations (100 micromolar); at low concentrations, tamoxifen does not effectively protect neurons in vitro or in vivo from excitotoxic permeability transition caused by glutamate (Ellerby et al., J. Neuroscience 17(16):6165-6178, 1997). Cell-specific responses of ANT may reflect cell-specific differences in oligomerization, i.e. the composition of multifunctional protein complexes comprising ANT. Cell-specific differences may include binding of ANT to alternative regulatory subunits from the family of ATP cassette-binding proteins (the regulatory subunit SUR may bind a large variety of potassium channels), or may reflect the expression of ANT isoforms. Interactions with creatin kinase and hexokinase render the ANT complex susceptible to the metabolic status of the respective cell. The paradigm of tamoxifen demonstrates that small molecules may modulate the signal transduction through ANT in a cell-specific manner, with the consequence of cell death.

Additional highly preferred target molecules for retinoids comprise connexins. Applicant has demonstrated that certain connexin isoforms are highly overexpressed in sinus node tissue undergoing apoptosis following administration of cis-configured retinoids. While connexin genes as targets of nuclear hormone receptors are well-established in the art, direct modulation of connexin function by cis-configured retinoids has not been taught so far. Connexins are a family of more than 20 proteins widely recognized for their function in forming channel-like intracellular junctions in a wide variety of tissues (including but not limited to heart, brain, skin, and also in cancer cells). The channels connect the cytoplasm of adjacent cells; between excitable cells, they participate in the formation of electrical synapses; between nonexcitable cells, they provide a morphological substrate for signal transduction (connexin function and related diseases are reviewed in White and Paul, Annual Reviews in Physiology 61:283-310, 1999). In the heart, different isoforms of connexins prevailing in different cell types serve the coordinated excitation of pacemaker cells and myocytes. Loss, inhibition, remodeling or redistribution of connexin-mediated channels leads to increased susceptibility to arrhythmias and sudden cardiac death (reviewed in: Jalife J, Morley G E, Vaidya D. Connexins and impulse propagation in the mouse heart, J Cardiovasc Electrophysiol. 10(12): 1649-63, 1999).

In myelinated fibers, connexins also participate in the formation and functional specification of axo-glial junctions in structures called paranodes which form the edge of the myelin sheath provided by individual Schwann cells, thus abutting the node of Ranvier (which is not covered by myelin). Schwann cell membranes in the vicinity of paranodes are enriched in inwardly rectifying potassium channels, and correspondingly, within 10 to 15 micrometer of the paranode, specialized regions exist in the axonal membrane that contain clusters of potassium channels. Thus, potassium channels and gap junctions are linked in a superstructure extending beyond the paranode that is thought to serve both cell attachment and intercellular signal transduction (reviewed in Scherer, Annals NY Acad. Sci. 883:131-142, 1999). More than 90 connexin-32 mutations have been identified as causative in a neurodegenerative demyelinating disease (x-linked Charcot-Marie-Tooth disease); several mutations permitted a residual partial activity. Since connexin channels are gated by voltage, interference with the voltage-dependent closure through retinoids (either directly or through ion channels participating in the superstructure) is contemplated to increase the open-time of the channel and thus assist in maintaining residual function. This residual function is likely to protect axons from complete demyelinization, and thus may mitigate neurodegeneration clinically.

Within a tumor, connexin-mediated channels may also exist between adjacent tumor cells; here, the block of connexin-mediated channels by retinoids is contemplated to damage and destroy tumor cells. Connexins may form a wide variety of channels: Through heterooligomeric interaction between different connexin isoforms within the same cell membrane, connexins may form heteromeric hemichannels; through heterooligomeric interaction between different connexin isoforms prsent in membranes of opposing cells, connexins may form heterotypic channels. All forms and types of connexin-mediated channnels are contemplated as targets for retinoids.

Since members of the ATP binding cassette protein family form a large variety of ion channels and transporters, or can bind to a large variety of ion channels and transporters, the specifications given for SUR would in principle apply to channels, transport proteins and their oligomeric complexes. Thus, further contemplated are all ion channels and transmembrane transporters, ion channels and associated regulatory subunits, growth factor receptors, enzymes, vesicular proteins, and scaffolding proteins bound in heterooligomeric configuration; small molecule transport channels such as amino acid transporters, lipid transporters, neurotransmitter transporters.

In a still further example, where the retinoid binds to xenobiotic transport protein of the ATP binding cassette (ABC) family, it is contemplated that administration of the retinoid may include modulation of a drug resistant phenotype in cancer cells (e.g., via interaction with the ABC in PgP or mdm proteins). It should further be appreciated that the modulation of the biological effect may comprise amplification or reduction of the biological effect.

Alternative Polypeptides:

It is still further contemplated that the retinoid may also bind to a cellular polypeptide other than an ion channel, and suitable alternative polypeptides include transmembrane proteins, membrane associated proteins, cytosolic proteins, proteins associated with or located within cellular compartments, including mitochondria, endoplasmatic reticulum, endosomes, and the nucleus. For example, particularly contemplated alternative cellular polypeptides include polypeptides binding inositol derivatives such as $PI_3$-kinase, Akt/protein kinase B, $PI_4$-kinase, $PI_{4,5}$-kinase, and inositol receptor isoforms. Also contemplated are P2x ion channels, which are regulated by extracellular ATP (Brake A J et al, New structural motif for ligand-gated ion channels defined by an ionotropic ATP receptor, Nature 371, 519-523, 1994), bcl-x and bcl-s. ITP (IDP)- and GTP (GDP)-binding proteins are particularly preferred over ATP (ADP)-binding proteins, and binding of cis-configured retinoids is particularly preferred over binding of all-trans-retinoids.

Yet further preferred targets comprise cytoskeletal proteins and lineage markers (both surface markers and intracellular markers), particularly in neuronal and muscular cell types (Applicant has demonstrated that cells particularly susceptible to cis-configured retinoids express the surface marker HNK1).

Since KATP can be regulated by ATP, ADP, and inositol phosphates, it would be expected that alternative signal transduction molecules binding ATP or inositol phosphates which act in a cell-specific manner would also qualify as targets for retinoids modulating signal transduction. Especially contemplated are kinases and phosphatases which are known to function in a highly cell-specific manner, further inositol-phosphate receptors and inositol-phosphate-metabolizing enzymes. Inositol binding often occurs through pleckstrin homology (PH) domains which are known to be structurally highly diverse, and are typically defined functionally through preferential binding of distinct inositol phosphate derivatives.

It has been demonstrated under a variety of experimental conditions (such as the influence of the inhibitor vanadate on electrophysiological recordings) that kinases and phosphatases directly and indirectly modulate ion channel activity. Kinases and phosphatases are also appreciated as highly cell-specific signal transduction molecules. For review of kinase cell-specificity, see for example Tasken et al., Structure, function, and regulation of human cAMP-dependent protein kinases, Adv. Second Messenger Phosphoprotein Res. 31:191-204, 1997; Tamai et al., Coupling signalling pathways to transcriptional control: nuclear factors responsive to cAMP, Recent Progr. Horm. Res. 52:121-139, 1997. For review of phosphatase cell specificity, see for example Brown and Hural, Functions of IL-4 and control of its expression, Crit. Rev. Immunol. 17(1):1-32, 1997; Koretzky, FASEB J. 7:420-426, 1993. For example, the kinase p38 has been established to participate in signaling of myocyte survival. Kinase pathways for cardiac myocyte survival have been reviewed by Latchman, Int. J. Exp. Pathol. 80(4c):189-196, 1999. Insulin secretion is controlled by kinase-dependent and phosphatase-dependent mechanisms (reviewed by Jones and Persault, Endocrine Reviews 19(4b):429-461, 1998). Different aspects of kinases and phosphatases in cancer cell growth control have been reviewed in considerable detail; for example, inhibition of cyclin-dependent kinase and cancer treatment (Garrett and Fattaey, Current Opinion in Genetics and Development 9:104-111, 1999); signal transduction inhibition in CNS tumors (Pollack et al., Pediatric Neurosurgery 29(5):228-244, 1998); inhibition of drug transport and chemoresistance (Lehne et al., Acta Oncologica 37(5):431-439, 1998). Thus, cell-specific modulation of kinase and phosphatase pathways by direct interaction with retinoids is contemplated to control biological responses including but not limited to cell growth, cell survival, arrhythmia and repolarisation, metabolism and endocrine responses, cancer cell apoptosis and chemosensitization. Kinases and phophatases of all substrate specificities are contemplated, including protein kinases and lipid kinases.

However, particularly excluded from appropriate alternative cellular proteins are RAR, RXR, and CRABP-I, CRABP-II, and visual pigments/retinoid isomerases in the vision pathway (Wald, G., Science 162, 230-239 (1968)). It should be recognized that alternative cellular polypeptides are not nuclear polypepides that act alone or in combination with another proteins as a transcription factor.

Further specifically contemplated for modulation by retinoid binding are enzymes, including phospholipases, lipoxygenases and cyclooxygenases, small GTP-binding proteins of the rho, ras, rac families), and factors interacting with small GTP-binding proteins.

Specifically contemplated as one mode of modulation are alterations in the structure of recognition surfaces utilized by interacting proteins along a signal transduction pathway; such alterations may be direct (by binding of a retinoid to a site participating in protein-ligand recognition, most often protein-protein-recognition) or indirect (by an allosteric effect on the conformation of one or more binding partners). The purpose of such alterations in the structure of recognition surfaces would be to alter a biological effect, including but not limited to modulation of metabolism and modulation of cellular proliferation (e.g. by altering interactions between insulin receptor and downstream effector molecules, or between EGF receptor and associated small GTP-binding proteins, and downstream effector molecules).

Based on the observation by Alvarez et al. (in: J. Biol. Chem. 270:5666-5673) that all-trans-retinoic acid is a potent transcriptional inducer of mitochondrial uncoupling protein, and further guided by the observation that the small amphiphilic compound hydroxy-nonenal may inhibit respiration in mitochondria (Humphries et al., Biochemistry 37:15835-15841, 1998), it is further contemplated that cis-configured retinoids, in distinction to all-trans-configured retinoids, may directly interact with mitocondrial uncoupler proteins. Such interactions, if tolerable side effects are observed, could lead to therapeutically useful compounds to treat obesity.

Consequently, a ligand-polypeptide complex is contemplated, that has a ligand comprising at least one of a retinoid and a retinoid metabolite, and that further has polypeptide other than a retinoic acid receptor, a retinoid X receptor, and a cellular retinoic acid binding protein, wherein the polypeptide binds the ligand with a dissociation constant of less than $10^3$/Mol, and wherein binding of the ligand to the polypeptide results in a modulation of a biological effect in a signal transduction pathway.

In further aspects of the inventive subject matter, it is contemplated that in alternative methods of cell-specifically interfering with a signal transduction pathway the system need not be limited to a mouse, and appropriate systems include in vivo and in vitro systems. For example, suitable in vitro systems include cell and tissue cultures, wherein the cells may be derived from a live specimen (e.g., biopsy), a secondary cell culture, or a thawed cell or tissue sample.

Particularly contemplated cells are mammalian cells, however, non-mammalian vertebrate and invertebrate cells are also contemplated. Especially contemplated in vivo systems include mammals (and particularly human), non-mammal vertebrates, and invertebrates (e.g., yeasts).

Administration of Retinoid:

With respect to the administration of the retinoid or retinoid metabolite, it is contemplated that a particular system will typically determine the particular administration. For example, where the system is a cell or tissue culture, the administration will typically comprise admixing a retinoid-containing solution to the cell or tissue culture. On the other hand, where the system is a human, mammal, or other animal, suitable administrations include oral or parenteral administration, injection, infusion, topical or transdermal application, etc. Likewise, it should be appreciated that the schedule of administration will predominantly depend on the particular system and biological effect, and it is therefore contemplated that the schedule may vary considerably. For example, while in some cell cultures a single administration will produce the desired modulation of the biological effect, administrations to a human may require multiple administrations to obtain the desired modulation of the biological effect.

Similarly, the dose of the retinoid or retinoid metabolite may vary substantially, depending on whether the target cell actively extracts and stores retinoids (such as Ito cells in the liver) in which case an exogenously added retinoid would experience substantial dilution that would require an increase in the initial dose of an exogenously given retinoid by at least one order of magnitude, if not more. However, it is preferred that the concentration of the retinoid in the system is between about 1 micromolar and about 10 millimolar. In further contemplated aspects of the inventive subject matter, it should be recognized that administration of contemplated retinoids or retinoid metabolites has a bimodal effect with respect to the amount of administered retinoids and retinoid metabolites. Among other effects, the inventor has observed that while administration of moderate amounts (i.e., 3-10 mg/kg) of 9-cis retinoic acid to mice leads to reduced growth of cardiomyocytes, cardiac neurons, and cells of the cardiac conductance system, administration of higher amounts (i.e., 20 mg/kg and higher, depending on batch purity) of 9-cis retinoic acid leads to reduced growth of cardiomyocytes, and apoptosis of cardiac neurons and cardiac pacemaker cells (cells belonging to the cardiac conduction system). Thus it is contemplated that retinoids and/or retinoid metabolites exhibit a bimodal activity. Consequently, it is contemplated that administration of a retinoid and/or retinoid metabolite at a first concentration has a modulation of a first biological effect, and administration of the retinoid and/or retinoid metabolite at a second concentration has a modulation of a second biological effect. Particularly contemplated first biological effects include reduction of growth in cardiomyocytes, and particularly contemplated second biological effects include induction of apoptosis in cardiac neurons and cardiac pacemaker cells (cells belonging to the cardiac conduction system).

Experimental Data

Animal Experiments:

1 week old litters of C57/b mice (around 3 g body weight) were divided into groups of five to 10 animals, to be treated with all-trans-RA in carrier, 9cis-RA in carrier, or carrier (canola oil, Sigma). Every treatment group was assigned to one nursing mother. Groups larger than 10 pups were avoided, to exclude limited feeding frequency as experimental variable. A retinoid preparation for gavage was formulated such that every animal received a maximum of 150 µl volume containing 40 mg/kg all-trans RA in carrier, 12 mg/kg or 20 mg/kg 9cis-RA in carrier, or carrier alone. DMSO or ethanol content was limited to 0.1%. Pups were gavage-fed from a tuberculin syringe connected with a bent vein catheter. The strong suckling reflex facilitated delivery of the viscous and odorous formulation. Depending on the territorial protection behaviour of the mother, pups were briefly rolled in cage stray after gavage to prevent triggering maternal infanticide behaviour through unusual smell of the pups. For two hours after gavage, pups were carefully monitored to prevent maternal infanticide. Every 24 h, the weight was recorded.

For uptake kinetics, pairs of treated pups were sacrificed by decapitation after 1 h, 2 h, 4 h, 8 h, 16 h, 24 h, 36 h and 72 h. Organs were removed under the dissection microscope and frozen in liquid nitrogen. Hearts were dissected under the surgical dissection microscope; tissues were divided into atria, ventricles, and enriched in conductance system (a tissue preparation containing the ventricular septa with the Purkinje fibers and the atrial region between the aorta and the pulmonal artery (outflow tract) with the sinus node). For immunohistology, pups were sacrificed after 72 h, hearts were rinsed in PBS, weighed and fixed in 4% para-formaldehyde in PBS before embedding in OCT for standard cryostat procedures. If pups were on the brink of death (typically between 36 and 72 h after gavage), they were sacrificed, and hearts were collected for confocal microscopy or HPLC.

Immunohistology:

For confocal microscopy, cryostat sections were first stained for apoptotic DNA strand breaks according to the TUNEL protocol (using the commercially available Apoptag™ kit, Oncor Inc., Gaithersburg Md.) and counterstained with rabbit anti-connexin37 antibody or rabbit anti-connexin40 antibody for conductance cells, or with rabbit anti-myosin antibody for cardiac myocytes. Immunodetection of connexin isoforms 40 and 43 has been established as a useful method to detect cells of the cardiac conductance system in rodents (Gourdie et al., The spatial distribution and relative abundance of gap-junctional connexin40 and connexin43 correlate to functional properties of components of the cardiac atrioventricular conducting system, J. Cell Science 105 (Pt 4) 985-991, 1993); because of the relatively weak signal of connexin40, the connexin isoform 37 can be used as equivalent marker for the conductance system in the mouse model (Willecke K et al, 1991; Willecke K, personal communication). The combination of rabbit anti-Neuron-specific enolase with propidium iodide followed published procedures (Current Protocols in Molecular Biology) and was used to identify cardiac neurons with advanced apoptotic condensation of nuclei. Procedures of immunohistology and image analysis are further described in detail in Graupner, WO 00/53236.

The mechanism of apoptosis was investigated using commercially available primary antibodies of highest purity, at dilutions recommended by the manufacturer, against IGF-1, IGF-II, the entire set of IGFbinding proteins (IGFBP1-5), IGF-R, mitochondrial Mn-dependent superoxide dismutase Mn-SOD, and cytoplasmic Cu/Zn-dependent superoxide dismutase Cu/Zn-SOD. Cellular phenotypes were identified with counterstain using cardiac myosin, actin, connexin37, connexin40, and connexin43 antisera. Confocal images were captured and processed for quantitative analysis by Zeiss LSM-300 software. Briefly, the pixel intensities per unit area amounting to channel background were determined for each antibody/secondary antibody combination and subtracted from the experimental pixel intensities. Pixel intensities per fluorescent channel in regions of high signal were normalized to pixel intensity per unit area, as were pixel intensities in control regions. At least five independent regions of similar size were analyzed per tissue type and retinoid treatment condition. Averaged pixel intensities per unit area upon 9cis retinoid induction were expressed as multiples of averaged pixel intensities per unit area in the absence of 9cis retinoid induction (fold induction +/−s.e.m.)

HPLC Analysis

Tissues collected for retinoid analysis were dispersed by two rounds of sonication. The slurry was doted with a known amount of synthetic retinoid to correct for variable extraction efficiencies between different samples. Extraction steps follow published procedures (see e.g. Biesalski, ibid.); after evaporation of the extraction solvents, the crude retinoid fraction was resuspended in HPLC buffer, injected on a RPC column and eluted with decreasing polarity in an isocratic gradient. The elution profiles were recorded and analyzed with system software; the positions of retinoic acid isoforms were identified, and absolute amounts of individual retinoids per mg tissue could be calculated.

Results:

The surprising bimodal effect, namely sudden death of mouse pups after 9cis-RA gavage of nonmutagenic amounts and the cardiac growth arrest, bears resemblance to growth factor withdrawal.

After application of high concentrations of 9cis-RA (20 mg/kg), a strong correlation was found between apoptosis and cellular clusters exhibiting conductance cell phenotype in regions of the mouse heart where the conductance system is typically located. The results of connexin40 staining and connexin37 staining were consistent. There was no correlation between apoptosis and conductance cell type after either high all-trans-RA application (40 mg/kg), lower concentrations of 9cis-RA (less than 10 mg/kg), or carrier application. No colocalization of TUNEL signal was found in cardiac myocytes after 9cis-RA treatment at either 20 mg/kg or less than 10 mg/kg, although the size of the average myocardial myocyte was reduced. The myocardial growth stunting seen at lower concentrations of 9cis-RA (less than 10 mg/kg) approached complete growth arrest around 10 mg/kg 9cis-RA, in contrast to the limited effect (less than 30% growth reduction) caused by substantially higher doses (40 mg/kg) of atRA. Detailed morphological assignments of IGF pathways to cardiac cell types by confocal microscopy reveals no indication for a correlation between interruption of IGF signaling and tissue-specific apoptosis. While IGFBP5, a known negative regulator of IGF-1 function, is moderately upregulated in cardiac myocytes after 9cis-RA treatment, the scope of the response is unlikely to account for the full picture of the growth arrest. No evidence was found for involvement of the fas ligand pathway.

Another observation with significant ramifications is the substantial activation of pathways metabolizing reactive oxygen species in cardiac tissue after administration of 20 mg/kg of 9cis-RA. First, upon addition of $H_2O_2$ in concentrations typically used to quench endogenous peroxidase activity, remarkable amounts of gas bubbles were released from large areas of myocardial cells in 9cisRA-treated tissue sections, but not in sections from animals treated with either all-trans-RA or carrier. This result is indicative for vastly increased amounts of endogenous peroxidase activity upon administration of high levels of 9cis-RA, and would be consistent with increased amounts of endogenous reactive oxygen species which are not be detectable by the methodologies applied. The pressure of the gas released lead to detachment of several tissue sections; by qualitative judgement, the amount of gas released was too high to be stored in, or produced by, conductance cells which are of very low abundancy compared to myocytes. Second, very high upregulation of MnSOD protein signal was detected in connexin-positive cells of the cardiac outflow tract; the signal of 3.4 fold upregulation localizes to the region of the atrium surrounding the sino-atrial node; the signal of 11 fold upregulation localizes most likely to the area of the sino-atrial node proper. Thus, apoptosis occurs in cells that have initiated a program to counteract the damaging effects of reactive oxygen species through upregulation of MnSOD at the protein level. Conversely, cardiac myocytes survive well with high levels of endogenous peroxidase activity and without elevated levels of enzymes protecting against reactive oxygen species. Thus, retinoid-induced apoptosis and enzymatic pathways producing and eliminating reactive oxygen are separate phenomena not causatively linked in the execution of programmed cell death in perinatal cardiac tissue.

Blood/Plasma, ventricles, atria and conductance cell region all contain the same types of retinoic acid isoforms in similar concentrations. The pharmacokinetic behavior of retinoic acid isoforms upon administration by gavage is substantially the same across all the cardiac tissues investigated. In summary, the HPLC data clearly refute the hypothesis that highly preferential uptake of retinoid into conductance cells, but not into cardiomyocytes, could account for the induction of tissue-specific apoptosis.

CONCLUSIONS

Thus, it should be recognized that contemplated methods particularly lend themselves to development and improvement of anti-diabetic drugs with reduced cardiac side-effects by selecting retinoid and retinoid analogs/derived compositions (which are preferably devoid of RXR agonist activity) that bind to SUR1, but not to SUR2. Likewise, it is contemplated to utilize retinoids and retinoid analogs/derived compositions to selectively modulate the function of SUR2 and thus generate novel compositions of channel-selective anti-arrythmic compounds. Another contemplated use of retinoids and retinoid analogs/derived compositions is the selective modulation of transport proteins for xenobiotica (xenobiotica include anti-tumor drugs), with the purpose to increase the susceptibility of highly drug-resistant tumors to antiproliferative therapy. Another contemplated use of retinoids is the selective modification of transport proteins affecting the mitochondrial permeability transition, with the purpose of effectively inducing apoptosis in aggressively growing tumors. Another contemplated use of retinoids is the selective modulation of neuronal activity, with the purpose of facilitating learning, and treating memory loss, psychosis, depression and behavioral consequences of drug abuse. Another contemplated use of retinoids is the mitochondrial uncoupling of energy metabolism through UCP isoforms, with the purpose of treating obesity.

Thus, specific embodiments and applications of cell specific modulations of signal transduction pathways have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of counteracting arrhythmia in a mammal comprising: administering 9-cis-retinoic acid to a mammal suffering from arrhythmia in a concentration effective to affect a signal transduction pathway which functionally includes a cellular polypeptide, which cellular polypeptide is a polypeptide other than a retinoic acid receptor, a retinoid X receptor, or a cellular retinoic acid binding protein, such that that the effect of the 9-cis-retinoic acid, on said cellular polypeptide of said pathway, results in counteracting the arrhythmia in the mammal.

2. The method of claim 1 wherein the cellular polypeptide comprises an ion channel protein, a sulfonyl urea receptor (SUR) or a complex of an ion channel protein and a SUR.

* * * * *

UNITED STATES PATENT AND TRADEMARK OFFICE
CERTIFICATE OF CORRECTION

PATENT NO.       : 7,605,185 B2                                             Page 1 of 1
APPLICATION NO. : 11/062222
DATED            : October 20, 2009
INVENTOR(S)      : Gerhart Graupner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 349 days.

Signed and Sealed this

Fifth Day of October, 2010

David J. Kappos
*Director of the United States Patent and Trademark Office*